(12) United States Patent
Griffin

(10) Patent No.: US 12,310,823 B2
(45) Date of Patent: *May 27, 2025

(54) SKIN PATCH FOR SUN PROTECTION AND METHOD OF MAKING

(71) Applicant: Gena M. Griffin, Laguna Beach, CA (US)

(72) Inventor: Gena M. Griffin, Laguna Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/594,286

(22) Filed: Mar. 4, 2024

(65) Prior Publication Data

US 2024/0261153 A1 Aug. 8, 2024

Related U.S. Application Data

(63) Continuation of application No. 17/363,322, filed on Jun. 30, 2021, now Pat. No. 11,950,983.

(60) Provisional application No. 63/046,909, filed on Jul. 1, 2020.

(51) Int. Cl.
| | |
|---|---|
| *A61F 13/00* | (2024.01) |
| *A61F 13/02* | (2006.01) |
| *A61F 13/0246* | (2024.01) |
| *B32B 7/06* | (2019.01) |
| *B32B 7/12* | (2006.01) |
| *B32B 25/20* | (2006.01) |
| *B32B 37/12* | (2006.01) |
| *B32B 38/00* | (2006.01) |
| *B32B 37/26* | (2006.01) |

(52) U.S. Cl.
CPC .. *A61F 13/00063* (2013.01); *A61F 13/00059* (2013.01); *A61F 13/00991* (2013.01); *A61F 13/025* (2013.01); *A61F 13/0266* (2013.01); *B32B 7/06* (2013.01); *B32B 7/12* (2013.01); *B32B 25/20* (2013.01); *B32B 37/12* (2013.01); *B32B 38/0036* (2013.01); *A61F 2013/00391* (2013.01); *A61F 2013/00544* (2013.01); *A61F 2013/00659* (2013.01); *B32B 2037/1253* (2013.01); *B32B 2037/268* (2013.01); *B32B 38/0004* (2013.01); *B32B 2307/71* (2013.01); *B32B 2307/732* (2013.01); *B32B 2319/00* (2013.01)

(58) Field of Classification Search
None
See application file for complete search history.

(56) References Cited

U.S. PATENT DOCUMENTS

| | | | | |
|---|---|---|---|---|
| 2,681,877 A | * | 6/1954 | Seymour | B44C 1/1733 |
| | | | | 156/304.6 |
| 11,950,983 B2 | | 4/2024 | Griffin | |

FOREIGN PATENT DOCUMENTS

| | | | | |
|---|---|---|---|---|
| GB | 2402884 A | * | 12/2004 | A61K 9/7084 |

OTHER PUBLICATIONS

English machine translation of EP 1452156 A1; Dufour; Sep. 1, 2004; 19 pages. (Year: 2004).*
English machine translation of KR 20170138778 A; Kim; Dec. 18, 2017; 21 pages. (Year: 2017).*
English machine translation of KR 20140039533 A; Chul; Apr. 2, 2014; 20 pages. (Year: 2014).*

* cited by examiner

*Primary Examiner* — Linda L Gray
(74) *Attorney, Agent, or Firm* — STETINA GARRED BRUCKER & NEWBOLES

(57) ABSTRACT

A skin patch for the UV protection is contemplated as being formed from a vulcanized silicone substrate, an adhesive gel coating adhered to the internal surface of the silicone substrate, and a release liner removably attached to the adhesive gel coating, wherein following removal of the release liner from the adhesive gel coating, the coating is operative to enable adherence of the skin patch to skin. The skin patch is further contemplated as being operative to at least partially absorb solar ultraviolet radiation via the vulcanized silicone substrate or the adhesive coating additionally comprising at least one UV-blocking compound having an absorption peak in the ultraviolet spectrum.

19 Claims, No Drawings

SKIN PATCH FOR SUN PROTECTION AND METHOD OF MAKING

CROSS-REFERENCE TO RELATED APPLICATIONS

This application is a continuation of U.S. patent application Ser. No. 17/363,322, filed Jun. 30, 2021, entitled SKIN PATCH FOR SUN PROTECTION, and claims benefit of U.S. Provisional Application No. 63/046,909, filed Jul. 1, 2020, and entitled ASSEMBLY PROCEDURE SUN PATCH, the contents of which are expressly incorporated herein by reference.

STATEMENT RE: FEDERALLY SPONSORED RESEARCH/DEVELOPMENT

Not Applicable

BACKGROUND

1. Technical Field

The present disclosure relates generally to the field of sun protection products. More particularly, the present disclosure relates to novel systems for silicone sun protection patches.

2. Related Art

In the field of cosmetics, there is a strong demand for improved products that are capable of addressing customer needs. Technology must develop the support this demand. Therefore, this is a need in the art for improved sun protection products such as silicone UV protection patches.

It is therefore important that new systems for silicone UV protection patches, and methods for producing those patches, be developed.

BRIEF SUMMARY

According to one embodiment for a skin patch for UV protection, a skin patch comprising a vulcanized silicone substrate, the vulcanized silicone substrate having an internal surface and an external surface, an adhesive gel coating adhered to the internal surface of the silicone substrate, and a release liner removably attached to the adhesive gel coating is contemplated, wherein following removal of the release liner from the adhesive gel coating, the adhesive gel coating is operative to enable adherence of the skin patch to skin. The skin patch is further operative to at least partially absorb solar ultraviolet radiation via the vulcanized silicone substrate or the adhesive gel coating comprising at least one UV-blocking compound having an absorption peak in the ultraviolet spectrum.

The vulcanized silicone substrate may comprise a heat cured rubber elastomer, or a cured liquid silicone rubber elastomer. The vulcanized silicone substrate may have a thickness of from about 0.010 inches to about 0.020 inches.

The adhesive gel coating may have a thickness of from about 0.005 inches to about 0.010 inches, and may comprise a silicone gel, which may comprise polydimethylsiloxane.

The release liner may have a thickness of about 0.002 inches to 0.007 inches, and may comprise a low-density polyethylene film.

The skin patch may be configured to be re-used via the adhesive gel coating substantially retaining the capability of being adhered to skin following it being detached from skin. The adhesive gel coating may also be adhered to the entirety of the internal surface of the silicone substrate, or may be adhered to only a portion of the silicone substrate.

The shape of the skin patch may also be configured so as to enhance adherence to a particular anatomical region of skin. The skin patch may be further operative to at least partially absorb ultraviolet radiation via the vulcanized silicone substrate or the adhesive gel coating additionally comprising at least one UV-blocking compound having an absorption peak in the ultraviolet spectrum. The UV-blocking compound may comprise zinc oxide.

The skin patch may also define a color configuration via the vulcanized silicone substrate or the adhesive gel coating additionally comprising one or more pigment compounds. The color configuration may be similar to the color configuration of a human skin tone, or may be dissimilar to the color configuration of a human skin tone. The skin patch may also define a color configuration via the vulcanized silicone substrate being substantially translucent or transparent, and the adhesive gel coating comprising the one or more pigment compounds. The pigment compounds, in certain embodiments, may also serve a dual functionality as a UV-blocking compound as well.

It is further contemplated that the skin patch may be further operative to at least partially absorb solar ultraviolet radiation within one or more of: the UVA spectrum, the UVB spectrum, the UVC spectrum. Additionally, it is contemplated that the skin patch may incorporate one or more interconnection elements for joining together two adjacent skin patches. For example, such interconnection elements may enable the skin patches to be stacked atop each other, in order to add further UV protection, or for the skin patches to be interconnected in a side-by-side fashion, so as to enable broader areas of skin to be covered by multiple skin patches while minimizing regions that are unprotected from UV radiation.

Methods for making a skin patch for treatment of UV protection are also contemplated. Such a method may comprise the steps of forming a vulcanized silicone substrate having an internal surface and an external surface, adhering an adhesive gel coating to the internal surface of the silicon substrate, and attaching a release liner to the adhesive gel coating, wherein during the step of forming the vulcanized silicone substrate, at least one UV-blocking compound having an absorption peak in the ultraviolet spectrum is incorporated with the vulcanized silicone substrate. It is also contemplated that the skin patch may further comprise a waterproofing compound for conferring water resistance to the skin patch.

According to exemplary embodiments of such a method, the vulcanized silicone substrate may be formed via one or more of: a platinum-catalyzed cure system, a condensation cure system, a peroxide cure system.

According to further refinements of such a method, the vulcanized silicone substrate, the adhesive gel coating, and the release liner are formed into a sheet, with the method further comprising the step of cutting the sheet into one or more individual skin patches. The step of cutting the sheet into one or more individual skin patches may also be configured to produce a skin patch having a shape configured to enhance adherence to a particular anatomical region of skin.

DETAILED DESCRIPTION

According to various aspects of the present disclosure, new and improved silicone UV protection patches are contemplated as being formed from a vulcanized silicone substrate, an adhesive gel coating adhered to the internal surface of the silicone substrate, and a release liner removably attached to the adhesive gel coating, wherein following removal of the release liner from the adhesive gel coating, the coating is operative to enable adherence of the skin patch to skin. Such skin patches are contemplated which are operative to at least partially absorb solar ultraviolet radiation via the vulcanized silicone substrate or the adhesive coating additionally comprising at least one UV-blocking compound having an absorption peak in the ultraviolet spectrum.

As presently contemplated, an exemplary embodiment of a skin patch may be generally formed of three components: a vulcanized silicone substrate, an adhesive gel coating, and a release liner. In the exemplary embodiment, the three components are arranged in a laminate layer-like arrangement, with the vulcanized silicone substrate having an external surface and an internal surface, the adhesive gel coating being adhered to the internal surface of the vulcanized silicone substrate, and the release liner being attached to the adhesive gel coating, such that the adhesive gel coating is in between the vulcanized silicone substrate and the release liner. The exemplary skin patch may thus be used by the wearer by removing the release liner, and adhering the adhesive gel coating to the skin, such that the external surface of the vulcanized silicone substrate will be facing outward, away from the wearer's skin, while the internal surface of the vulcanized silicone substrate will be facing inward, towards the wearer's skin.

The vulcanized silicone substrate may be formed of any vulcanized silicone suitable for use as a substrate material in a skin patch. In the exemplary embodiment, the vulcanized silicone substrate is formed from a heat cured rubber (HCR) silicone elastomer, also referred to as high consistency rubber silicone, which is an elastomeric polymer formed from high molecular weight chains of a silicone elastomer, typically polymethylhydrosiloxane. Generally, the HCR silicone elastomer is provided in the form of gummy, solid, high viscosity sheets that are combined with a crosslinker and/or a catalyst, thoroughly combined in a mill, formed into the desired shape, and once in the desired shape, cured via the addition of heat in a process called vulcanization to produced vulcanized silicone. However, it may also be seen that in other embodiments, the vulcanized silicone substrate may be formed from a liquid silicone rubber (LSR) elastomer. The process of producing a vulcanized silicone substrate from an LSR elastomer may be seen to be chemically similar to the process of vulcanized silicone production using an HCR elastomer, except that where HCR is generally an elastomeric polymer provided in the form of a solid sheet, the elastomeric polymer provided in an LSR process is generally provided in the form of a thick viscous liquid, which may require different techniques or equipment, and which may be more or less advantageous for producing certain types of components. Both processes may have advantages and disadvantages, but it may be seen that both may be seen to be suitable for producing a vulcanized silicone substrate according to the present disclosure, along with other known and later discovered processes for producing a vulcanized silicone substrate suitable for use in a skin patch.

According to the exemplary embodiment, the vulcanized silicone substrate of the present disclosure is contemplated to have a thickness of from about 0.010 inches to about 0.020 inches. However, it may be seen that in other embodiments, the vulcanized silicone substrate may have other thicknesses, and it further may be seen that the vulcanized silicone substrate may have variation in thickness. For example, the vulcanized silicone substrates of different skin patches may be thicker or thinner, as required, or even a single vulcanized silicone substrate of a single skin patch may be optionally thicker in one location and thinner in another, in order to better adapt to better adapt the skin patch to the contours of the anatomy of the underlying skin to which the skin patch is to be attached.

The adhesive gel coating may be formed of any adhesive gel which may be attached to a vulcanized silicone substrate, and which may be suitable to adhere to skin. In the exemplary embodiment, the adhesive gel may comprise an organosilicon compound such as polydimethylsiloxane. Adhesive gels suitable for skin-contact applications are well characterized in the art, and it may be seen that any known or future developed adhesive gel may be seen to be suitable for producing an adhesive gel coating suitable for use in a skin patch according to the present disclosure. In the exemplary embodiment, the adhesive gel coating may have a thickness of from about 0.005 inches to about 0.010 inches. However, it may be seen that in other embodiments, the adhesive gel coating may have other thicknesses. For example, the adhesive gel coating of different skin patches may be thicker or thinner, as required, or even a single adhesive gel coating of a single skin patch may be optionally thicker in one location and thinner in another, in order to better adapt to better adapt the skin patch to the contours of the anatomy of the underlying skin to which the skin patch is to be attached.

It is further contemplated that the adhesive gel coating may be configured in a variety of ways in order to confer various characteristics to the skin patch. For example, it may be seen that the adhesive gel coating may be adhered to the entirety of the internal surface of the silicone substrate, which may be preferred in certain embodiments, or may be adhered to only portions or regions of the internal surface of the silicone substrate. It may thus be seen that such variation may affect the adherence characteristics of the skin patch, enabling the skin patch to be used according to different ways, in order to enhance the utility of the skin patch. Further, it may be seen that the adhesive gel coating may be formulated in order to enable the skin patch to be used once, or to be used multiple times. For example, in certain circumstances it may be desired to formulate the adhesive gel coating in order to enable the skin patch to be used more than once, via the adhesive gel coating not substantially having its capability of being adhered to skin substantially degraded following being detached from skin. Alternatively, it may be desirable to formulate an adhesive gel coating which is only suitable for a single use, and in which the adhesive gel coating may be substantially reduced in its capability to re-adhere to skin following detachment from skin. It may be seen that this capability may be accomplished via known or future developed methods of formulating a adhesive gel coating Likewise, it may be seen that the skin patch may be configured with a waterproofing compound in order to confer a water resistance property to the skin patch. For example, it may be seen that by formulating one or more of the silicone substrate or the adhesive gel so as to a waterproofing compound, such as a hydrophobic material, that component may be rendered substantially more resistant to water penetration, and as such, may prevent water from migrating to regions under the skin patch. Alternatively, such waterproofing compound may instead constitute a further layer of waterproofing material, such as a layer atop the silicone substrate, or between the silicone substrate and the adhesive gel, which may permit the skin patch to continue functioning according to its desired functionality and may further function to prevent or inhibit water penetration therethrough. Likewise, it is further contemplated that waterproofing compounds may only be added in relation to certain portions of the skin patch, and not others, so as to confer waterproofing characteristics to only certain portions of the skin patch. According to certain exemplary embodiments, the waterproofing compound may comprise a vapor-permeable, water-impermeable membrane or coating such as expanded polytetrafluoroethylene (ePTFE) over, underneath, or within the silicone substrate. Other types of waterproofing compounds are also contemplated, and may include any compound known or future developed which may be used in conjunction, in any fashion, with the contemplated skin patch in order to confer a water resistance property thereto, or to portions thereof.

The release liner may be formed of any material which is suitable to be attached to an adhesive gel coating and to be released therefrom to expose the adhesive gel coating in order to enable the adherence the skin patch to skin. In the exemplary embodiment, the release liner comprises a low-density polyethylene film. However, it may be seen that in other embodiments, the release liner may be formed of any known or future developed material which may be suitable for use in a skin patch. So long as the release liner accomplishes its function of preventing unintended adhesion or degradation of the adhesive characteristics of the adhesive gel prior to removal of the release liner and use of the skin patch, any material may be suitable for use as a release liner. In the exemplary embodiment, the release liner has a thickness of about 0.005 inches. However, in other embodiments, the release liner may be thicker or thinner, such as between 0.002 to 0.007 inches, and it may be seen that the release liner may be any thickness without departing from the scope and spirit of the present disclosure.

The skin patch may be configured in order to enable adherence to a particular anatomical region of skin. According to the exemplary embodiment, such configurations may be via, for example but without limitations, producing a skin patch having a particular predefined shape, which may be in two dimensions or in three dimensions, or in producing a skin patch having particular predefined regions such as creases, folds, curves, pre-perforated regions for allowing the optional reduction in size of the skin patch, etc. For example, a skin patch may be produced which may be configured to adhere to the region of skin on a wearer's face underneath a wearer's eye, which may necessitate the production of a skin patch having an arcuate curvature, or even a topological manifold shape. It is further contemplated that skin patches may be produced in order to not only generally match a particular anatomical region of skin which may be a common region of application, or that skin patches may be produced in particular sizes or configuration which may be sized and shaped to fit particular different anatomical subsets of individual so that a particular individual may learn their particular "size" and "shape" configuration and subsequently purchase additional skin patches according to their particular size and shape, but also that skin patches may be custom-produced for particular individuals in order to be uniquely tailored to fit the anatomical features of that individual.

It is further contemplated that the skin patch may be further operative to at least partially absorb solar ultraviolet radiation via the vulcanized silicone substrate or the adhesive gel coating additionally comprising at least one UV-blocking compound having an absorption peak in the ultraviolet spectrum. Solar ultraviolet (UV) radiation is the light from the sun and other sources of UV radiation such as tanning beds that causes sunburn, skin aging, and DNA damage, which may heighten the risk of developing skin cancers. Ultraviolet radiation generally lies between 10 and 400 nanometers on the electromagnetic spectrum. Because the Earth's atmosphere generally blocks most UV radiation wavelengths from the sun below 200 nanometers, most commercial sunscreens are configured to generally absorb and block UV radiation between 200 and 400 nanometers via containing one or more UV-blocking components which may have absorption peaks within this range, with some sunscreens containing multiple UV-blocking components with different absorption peaks in order to confer broader protection across the UV spectrum.

Generally, solar radiation within the UV spectrum is subdivided between three categories: UV A, UV B, and UV C. UV A radiation, the longest-wave, lowest energy UV light, and generally lies between 315 and 400 nm. Radiation within the UV A spectrum is the most commonly encountered from sunlight, penetrates most deeply into skin, and is considered to be most responsible for tanning as well as premature skin aging changes, including wrinkle formation. Radiation within the UV B spectrum lies between 280 and 315 nm, and is less frequently encountered from sunlight. UV B radiation penetrates less deeply into skin, but are higher in energy than radiation within the UV A spectrum. UV B radiation is most responsible for producing sunburn and skin damage that may result in skin cancers. Radiation within the UV C spectrum, which is between 100 and 280 nm, is almost never encountered from sunlight, because it is nearly entirely filtered out by the Earth's ozone layer and atmosphere. UV C is the most energetic type of UV light, and is commonly used is disinfectant lamps. Skin exposure to UV C radiation may cause burns or other injury. Most sunscreen products sold today incorporation combinations of UV-blocking components which function to block at least UV rays within the UV A and UV B spectrum.

Thus, via incorporating one or more UV-blocking component into the vulcanized silicone substrate or the adhesive gel coating, it is contemplated that the skin patch may be further operative to at least partially absorb solar radiation and thus confer UV-protective properties to the region of skin to which the skin patch has been adhered. For example, in the exemplary embedment, it is contemplated that the UV blocking compound may comprise zinc oxide. However, in other embodiments, it is contemplated that the UV-blocking compound may be other compounds, including but not limited to aminobenzoic acid, avobenzone, cinoxate, dioxybenzone, ecamsule, homosalate, menthyl anthrinalte, octocrylene, octyl methoxycinnamate, octyl salicylate, oxybenzone, padimate o, phenylbenzimidazole, suslisobenzone, titanium dioxide, and/or trolamine salicylate. It may be that, according to the particular characteristics of the silicone substrate or the adhesive gel coating, a particular UV-blocking compound or combinations of UV-blocking compounds may be preferred.

It is further contemplated that the skin patch may define a color configuration via the vulcanized silicone substrate or the adhesive gel coating additionally comprising one or more pigment compounds. Color or a color combination may be an important feature for the contemplated skin patch for a number of reasons. For example, it may be preferred that the skin patch be aesthetically designed with a color or a combination of colors and other features in order to be visually similar to the color configuration of a human skin tone, so that it may become difficult to visually distinguish, without close inspection, that the wearer is wearing a skin patch. In order to accomplish this in a fashion such that many different individuals may be able to purchase skin patches which closely match their particular skin tone, it may be necessary to produce skin patches in many different skin tone versions and to subsequently allow customers to purchase the version which best matches their skin tone. Alternatively, it may be desirable to produce a skin patch having a color configuration which is dissimilar to a human skin tone, so that the fact that a wearer is wearing a skin patch is readily apparent, or even becomes highly noticeable. For example, it may be aesthetically desirable to wear a skin patch having a particular color or color scheme to indicate a wearer's support or loyalty to a particular cause or organization, such as an athletic team, or it may be simply desirable to wear a skin patch having a particular color configuration for purely aesthetic reasons. Furthermore, it may be desirable for the skin patch to incorporate on the external surface of the vulcanized silicone substrate certain particular colors, designs, words, or imagery. For example, it may be desirable for a corporate entity to have skin patches produced which has a corporate logo on the external surface of the vulcanized silicone substrate, and to distribute those skin patches in order to advertise the corporation's products or services. Being customizable, it is readily envisioned that there are many purposes which may be accomplished via having different color configurations defined by the skin patch including one or more pigment compounds. For example, it may even be contemplated that the skin patch may include one or more fluorescent pigment compounds, which may result in the skin patch illuminating when exposed to ultraviolet light. Thus, it is envisioned that a skin patch which incorporates both a UV-blocking compound and a fluorescent pigment compound which illuminates in response to UV light may thus indicate via illumination when the UV-blocking compound is effectively screening out UV light to the underlying region of skin.

For example, in the exemplary embodiment, it is contemplated that colors such as hot pink, electric blue, green, or yellow may be produced via the introduction of commercially available pigments in the above described fashion, such as Pantone 806 C for hot pink, Pantone 2925 C for electric blue, Pantone 802 C for green, and Pantone 809 C for yellow. These pigments may be used in conjunction with UV blocking components as well. It is further contemplated that the pigment may also function as a UV blocking compound, so that a single compound may serve multiple purposes. It may also be seen that the vulcanized silicone substrate itself may be formulated so as to be substantially translucent or transparent, in whole or in part (which may include translucent regions), and that the color scheme may arise as a result of the underlying adhesive gel incorporating pigments which may be seen through the transparent or translucent vulcanized silicone substrate.

It is also contemplated that the skin patches may incorporate an interconnection element in order to permit adjacent skin patches to be interconnected, so as to enhance UV-protective features or for other purposes. In certain embodiments, it may be contemplated that such interconnection elements may be, for example but without limitation, cutouts on the sides of the skin patches that are configured to interconnect horizontally with protruding regions on the sides of skin patches placed on an adjacent region of skin, much in the same way that puzzle pieces interconnect. Such interconnection features may permit, for example, greater areas of skin to be protected from UV radiation without leaving substantial gaps between adjacently placed skin patches, which may result in sunburns or other skin damage in the gap regions. It may further be seen that without an interconnection element, in regions of skin that are prone to motion during activities of the wearer, even carefully placed skin patches in adjacency may be prone to developing or having such gaps exposed during wear, and as such, interconnection elements may be desirable to mitigate or prevent the formation of such gaps. However, it may also be seen that other interconnection schemes and elements are possible. For example, it is also contemplated that the skin patches may be vertically stacked atop each other in order to enhance UV protection, and that such interconnection elements may be as simple as the adhesive gel being configured to adhere to the external surface of a vulcanized silicone substrate. It should be appreciated that any known or future developed interconnection element may be utilized, as long as such interconnection is achieved, including combinations of interconnection elements or schemes.

Methods of making there herein contemplated skin patches are also contemplated, comprising the steps of forming a vulcanized silicone substrate having an internal surface and an external surface, adhering an adhesive gel coating to the internal surface of the silicone substrate, and attaching a release liner to the adhesive gel coating. Formation of the vulcanized silicone substrate is contemplated as being accomplished via any known or future developed method of forming a vulcanized silicone substrate, including but not limited to a platinum-catalyzed cure system, a condensation cure system, or a peroxide cure system. According to the exemplary embodiment, the vulcanized silicon substrate is formed from a platinum-catalyzed HCR cure system whereby the HCR compound is mixed together with the catalyst in a mill. Optionally at this time, one or more pigments and/or one or more UV blocking agents may be added to the composition prior to the vulcanization of the mixed HCR compound and catalyst. In the exemplary embodiment, titanium dioxide is added at this time. A slab mold is then prepared with a mold release agent, and the mixed composition is then laid out or otherwise dispensed into a slab mold at a thickness of between 0.010 to 0.020 inches and the mixed composition is then vulcanized in a vulcanization press at 300 F and 80 PSI for 5 minutes. The slab is subsequently demolded and trimmed as necessary and washed to remove any mold release still attached to the slab. In embodiments in which LSR is used instead of HCR, the LSR mixture may be mixed in a mixing apparatus other than a mill, at which time one or more pigments and/or one or more UV blocking agents may be added to the composition, and the resulting composition may be dispensed into the slab mold, rather than laid out. The remaining steps may be the same.

The step of adhering an adhesive gel coating to the vulcanized silicone substrate may be accomplished via any known or future method of adhering an adhesive gel coating to a vulcanized silicone slab. In the exemplary embodiment, this step may be performed via placing the vulcanized silicone substrate onto a flat surface, adding shims to the side of the substrate, and pouring silicone gel into the center of the slab. A screed is used to level the gel in order to define the thickness of the gel according to the height of the shims used. The assembly may then be cured in an oven at sufficient time and temperature to adhere the gel to the silicone substrate and to heat cure the gel.

The step of attaching a release layer to the adhesive gel coating may be performed according to any known or future developed method of attaching a release layer to an adhesive gel coating. In the exemplary embodiment, the step is performed via manually attaching the release layer, which is a low-density polyethylene film, atop the adhesive gel coating. However, it may be seen that in other embodiments, other types of release layers other than low-density polyethylene films, and other ways of attaching the release layer may be utilized, without departing from the scope and spirit of the present disclosure.

Following the attachment of the release layer, it is contemplated that the formed resulted laminated material comprising the vulcanized silicone substrate, the adhesive gel, and the release layer may itself not form the final product, but rather may be a bulk sheet component which is then cut into one or more skin patches, according to predefined cutting configurations configured to produce one or more skin patches. For example, a simple die cutter may result in the sheet being divided into many identical rectangular skin patches. However, it may also be seen that more complex cutting configurations may be envisioned in which more complex shapes may result, such as shapes configured to match particular anatomical features or regions of skin of the typical wearer. This step may, for example, be configured to produce a particular type of skin patch which defines a shape configured to enhance adherence to a particular region of skin. For example, it may be envisioned that a skin path cut into a crescent-moon shape may be beneficial for use in the region of skin below a wearer's eye, whereas a normal rectangular or square skin patch would not be ideal for sustained adherence. However, it is also contemplated that a large variety of shapes may be achievable, as well as more complex configurations, without departing from the scope and spirit of the present disclosure.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the exemplary embodiments.

What is claimed is:

1. A method of making a skin patch for UV protection, the method comprising the steps of:
    forming a vulcanized silicone substrate having an internal surface and an external surface;
    adhering an adhesive gel coating to the internal surface of the silicone substrate; and
    attaching a release liner to the adhesive gel coating;
    wherein during the step of forming the vulcanized silicone substrate, at least one UV-blocking compound having an absorption peak in the ultraviolet spectrum is incorporated with the vulcanized silicone substrate; and
    wherein the adhesive gel coating consists of an adhesive gel.

2. The method of claim 1, wherein the vulcanized silicone substrate has a thickness of from about 0.010 inches to about 0.020 inches.

3. The method of claim 1, wherein the vulcanized silicone substrate comprises a heat cured rubber elastomer.

4. The method of claim 1, wherein the vulcanized silicone substrate comprises a cured liquid silicone rubber elastomer.

5. The method of claim 1, wherein the adhesive gel coating has a thickness of from about 0.005 inches to about 0.010 inches.

6. The method of claim 1, wherein the adhesive gel comprises polydimethylsiloxane.

7. The method of claim 1, wherein the skin patch is configured to be re-used via the adhesive gel coating substantially retaining a capability of being adhered to skin following the adhesive gel coating being detached from skin.

8. The method of claim 1, wherein the adhesive gel coating is adhered to the entirety of the internal surface of the silicone substrate.

9. The method of claim 1, wherein the adhesive gel coating is adhered to only a portion of the internal surface of the silicone substrate.

10. The method of claim 1, wherein the release liner has a thickness of about 0.002 inches to about 0.007 inches.

11. The method of claim 1, wherein the skin patch is further operative to at least partially absorb solar ultraviolet radiation within one or more of: the UVA spectrum, the UVB spectrum, the UVC spectrum.

12. The method of claim 11, wherein the UV-blocking compound comprises zinc oxide.

13. The method of claim 1, wherein the skin patch further comprises a water-proofing compound.

14. The method of claim 1, wherein the vulcanized silicone substrate is formed via one or more of: a platinum-catalyzed cure system, a condensation cure system, a peroxide cure system.

15. The method of claim 1, wherein the step of adhering the adhesive gel coating to the internal surface of the silicone substrate comprises a heat-curing step.

16. The method of claim 1, wherein the skin patch defines a color configuration via the vulcanized silicone substrate additionally comprising one or more pigment compounds.

17. The method of claim 16, wherein the one or more pigment compounds are further operative to at least partially absorb solar ultraviolet radiation within one or more of: the UVA spectrum, the UVB spectrum, the UVC spectrum.

18. The method of claim 16, wherein the one or more pigment compounds illuminate when said skin patch is exposed to ultraviolet light.

19. The skin patch produced from the method of claim 1.

* * * * *